(12) United States Patent
Zollmann et al.

(10) Patent No.: US 11,154,337 B2
(45) Date of Patent: Oct. 26, 2021

(54) SPINAL SCREW HANDLING

(71) Applicant: Medos International Sarl, Le Locle (CH)

(72) Inventors: Veronique C. Zollmann, Gebenstorf (CH); Laura Wilson, Basel (CH); Jan Klett, Aesch (CH); Roger Berger, Büren (CH); Peter Senn, Waldenburg (CH)

(73) Assignee: MEDOS INIERNATIONAL SARL, Le Locle (CH)

( * ) Notice: Subject to any disclaimer, the term of this patent is extended or adjusted under 35 U.S.C. 154(b) by 194 days.

(21) Appl. No.: 16/286,188

(22) Filed: Feb. 26, 2019

(65) Prior Publication Data
US 2020/0268420 A1    Aug. 27, 2020

(51) Int. Cl.
*A61B 17/70* (2006.01)
*A61B 17/86* (2006.01)
*A61B 17/56* (2006.01)

(52) U.S. Cl.
CPC ...... *A61B 17/7082* (2013.01); *A61B 17/7059* (2013.01); *A61B 17/86* (2013.01); *A61B 2017/564* (2013.01)

(58) Field of Classification Search
CPC ...... A61B 17/70; A61B 17/7074–7077; A61B 17/88; A61B 17/8841; A61B 17/8875–8894
See application file for complete search history.

(56) References Cited

U.S. PATENT DOCUMENTS

| | | |
|---|---|---|
| 5,445,641 A | 8/1995 | Frigg et al. |
| 6,328,746 B1 | 12/2001 | Gambale |
| 7,406,899 B2 | 8/2008 | Walker |
| 7,461,574 B2 | 12/2008 | Lewis et al. |
| 7,771,429 B2 | 8/2010 | Ballard et al. |
| 8,079,468 B2 | 12/2011 | Pleil et al. |
| 8,087,325 B2 | 1/2012 | Neubardt |
| 8,105,328 B2 | 1/2012 | Protopsaltis |
| 8,328,823 B2 | 12/2012 | Aranyi et al. |
| 8,414,594 B2 | 4/2013 | Berger et al. |

(Continued)

FOREIGN PATENT DOCUMENTS

WO    00/07510 A1    2/2000

OTHER PUBLICATIONS

"Invitation to Pay Additional Fees Received for PCT Patent International Application No. PCT/IB2020/051361", dated May 14, 2020, 14 pages.

*Primary Examiner* — Eduardo C Robert
*Assistant Examiner* — Michelle C Eckman
(74) *Attorney, Agent, or Firm* — Mintz Levin Cohn Ferris Glovsky and Popeo, P.C.

(57) ABSTRACT

Various exemplary methods and devices are provided for the delivery of spinal screws to a spinal implant site. A variety of exemplary configurations and implementations are provided, but, in general, a handheld tool is provided having a guide member with a lumen formed therein that is configured to deliver a spinal screw to a cervical spine implant. The tool can include various features that facilitate the delivery of the spinal screw to the implant. The tool can include a storage component, such as a magazine, that is configured to hold a plurality of spinal screws for delivery of multiple spinal screws during a surgical procedure.

20 Claims, 12 Drawing Sheets

(56) References Cited

U.S. PATENT DOCUMENTS

| | | |
|---|---|---|
| 8,628,537 B2 | 1/2014 | Ciccone et al. |
| 8,662,299 B2 | 3/2014 | Pratt et al. |
| 8,845,697 B2 | 9/2014 | Montello et al. |
| 8,943,927 B2 | 2/2015 | Watt |
| 8,979,874 B2 | 3/2015 | Darois et al. |
| 9,271,725 B2 | 3/2016 | Colesanti et al. |
| 9,271,732 B2 | 3/2016 | Walker |
| 9,284,110 B2 | 3/2016 | Garcia et al. |
| 9,332,983 B2 | 5/2016 | Shipp |
| 9,510,886 B2 | 12/2016 | Giersch et al. |
| 9,572,611 B2 | 2/2017 | Wand |
| 9,801,633 B2 | 10/2017 | Sholev et al. |
| 9,918,755 B2 | 3/2018 | Bootwala et al. |
| 9,956,009 B1 | 5/2018 | Shoshtaev |
| 2004/0243139 A1* | 12/2004 | Lewis ............... A61B 17/8891 606/104 |
| 2007/0119871 A1 | 5/2007 | Garcia |
| 2011/0130767 A1* | 6/2011 | Watt .................. B25B 23/101 606/104 |
| 2013/0304135 A1* | 11/2013 | Giersch ............. A61B 17/8872 606/304 |
| 2017/0087697 A1 | 3/2017 | Garcia et al. |
| 2019/0046251 A1* | 2/2019 | Detweiler .......... A61B 17/8872 |

\* cited by examiner

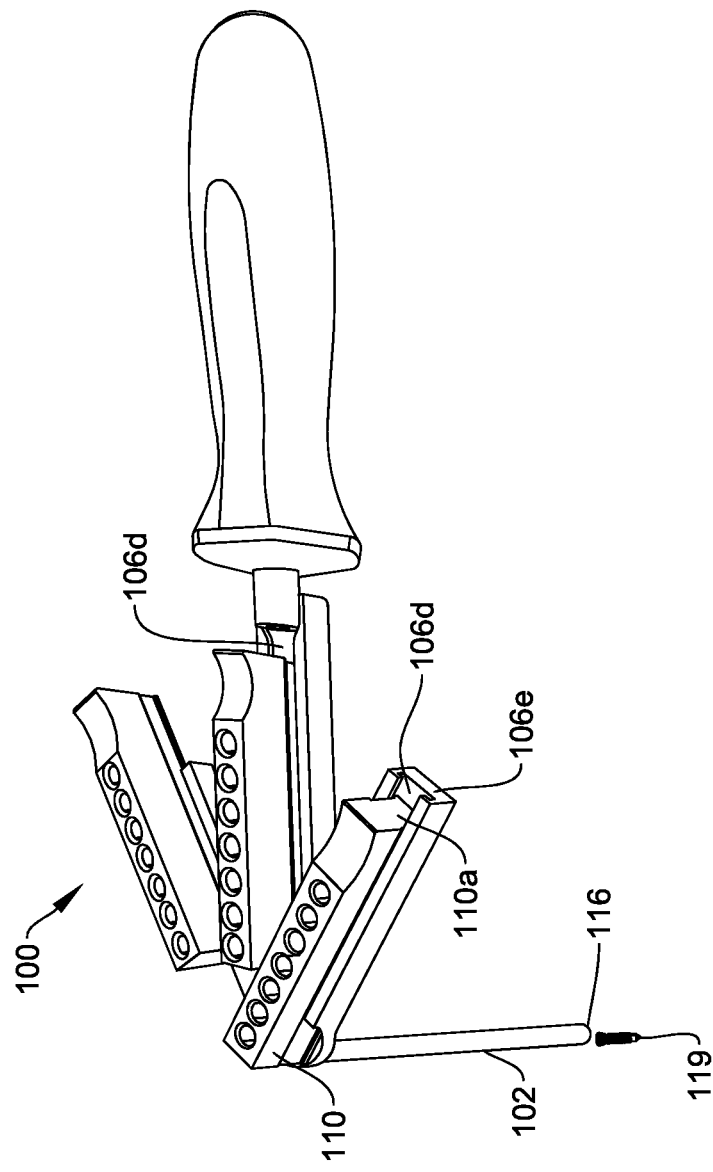
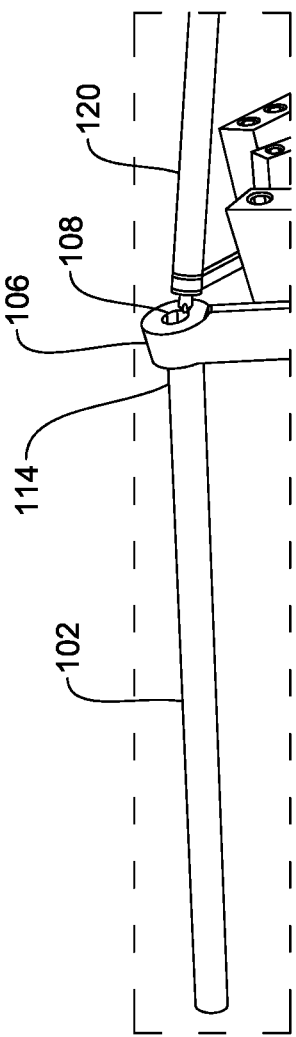

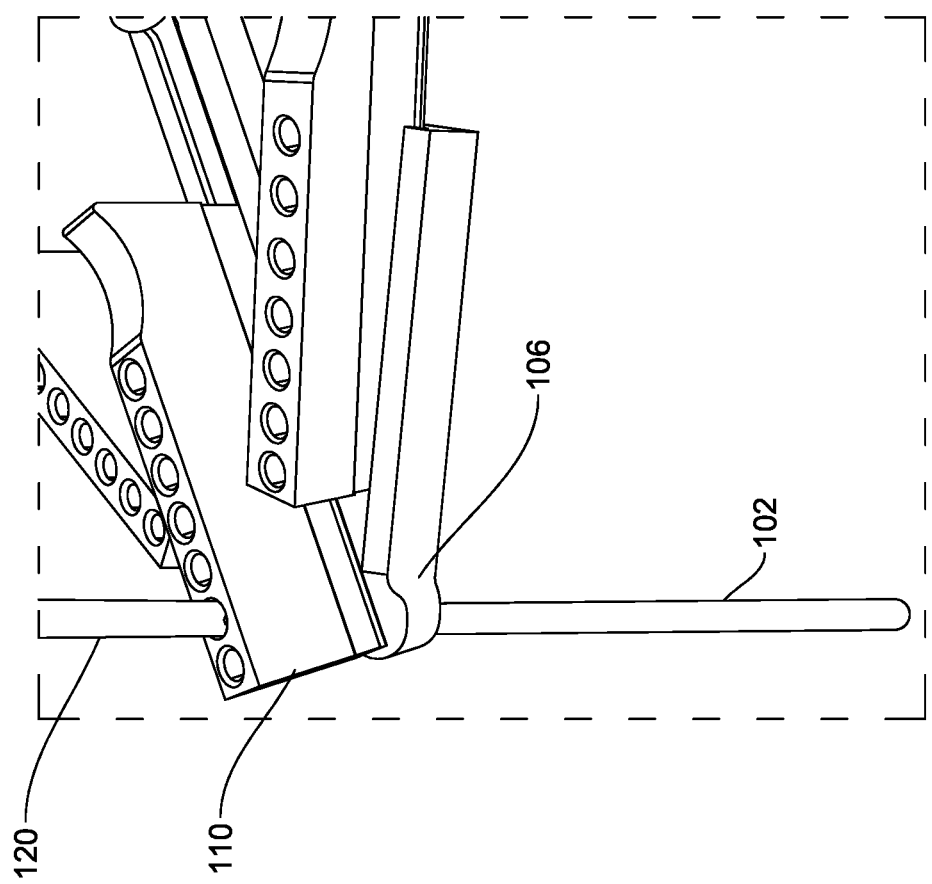

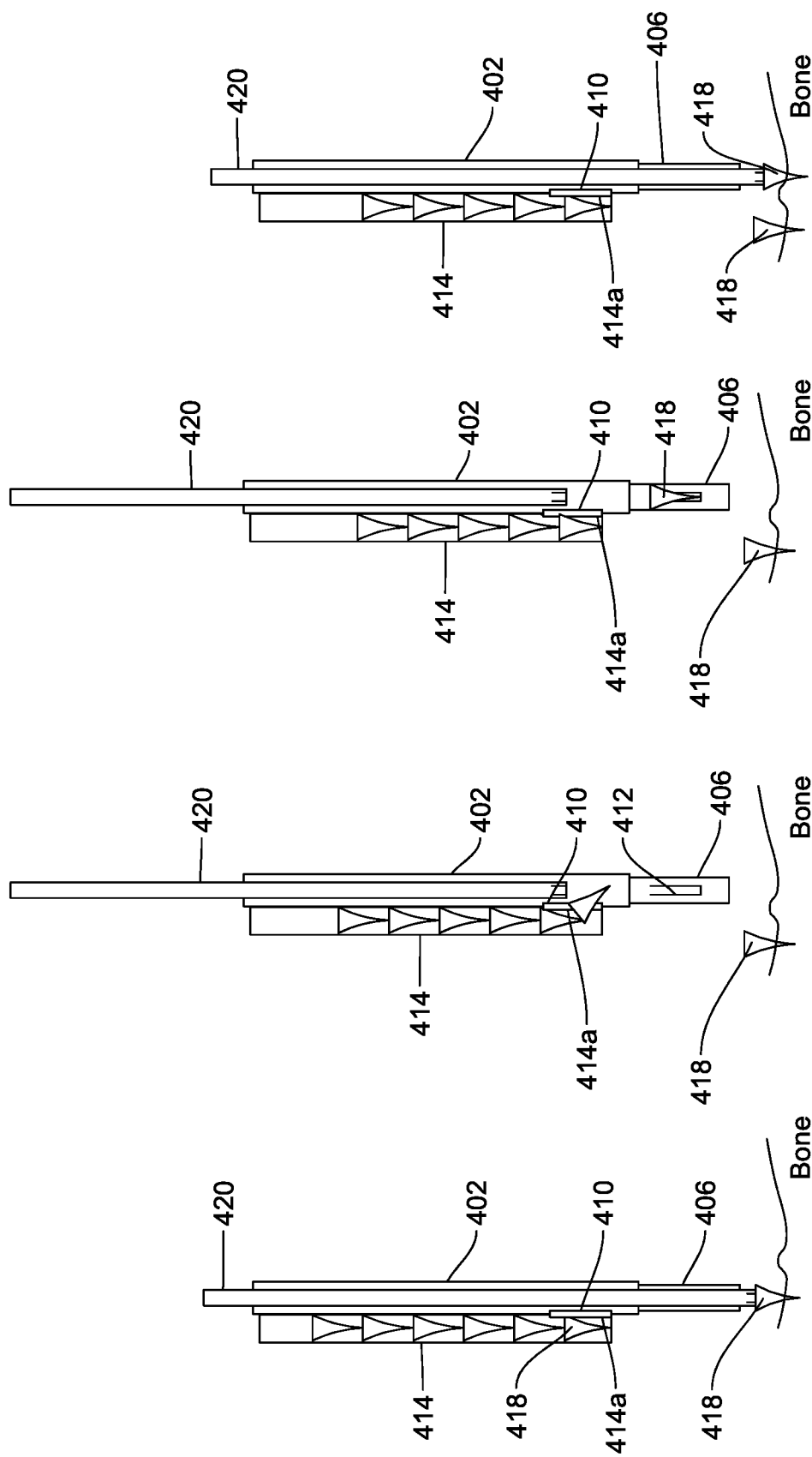

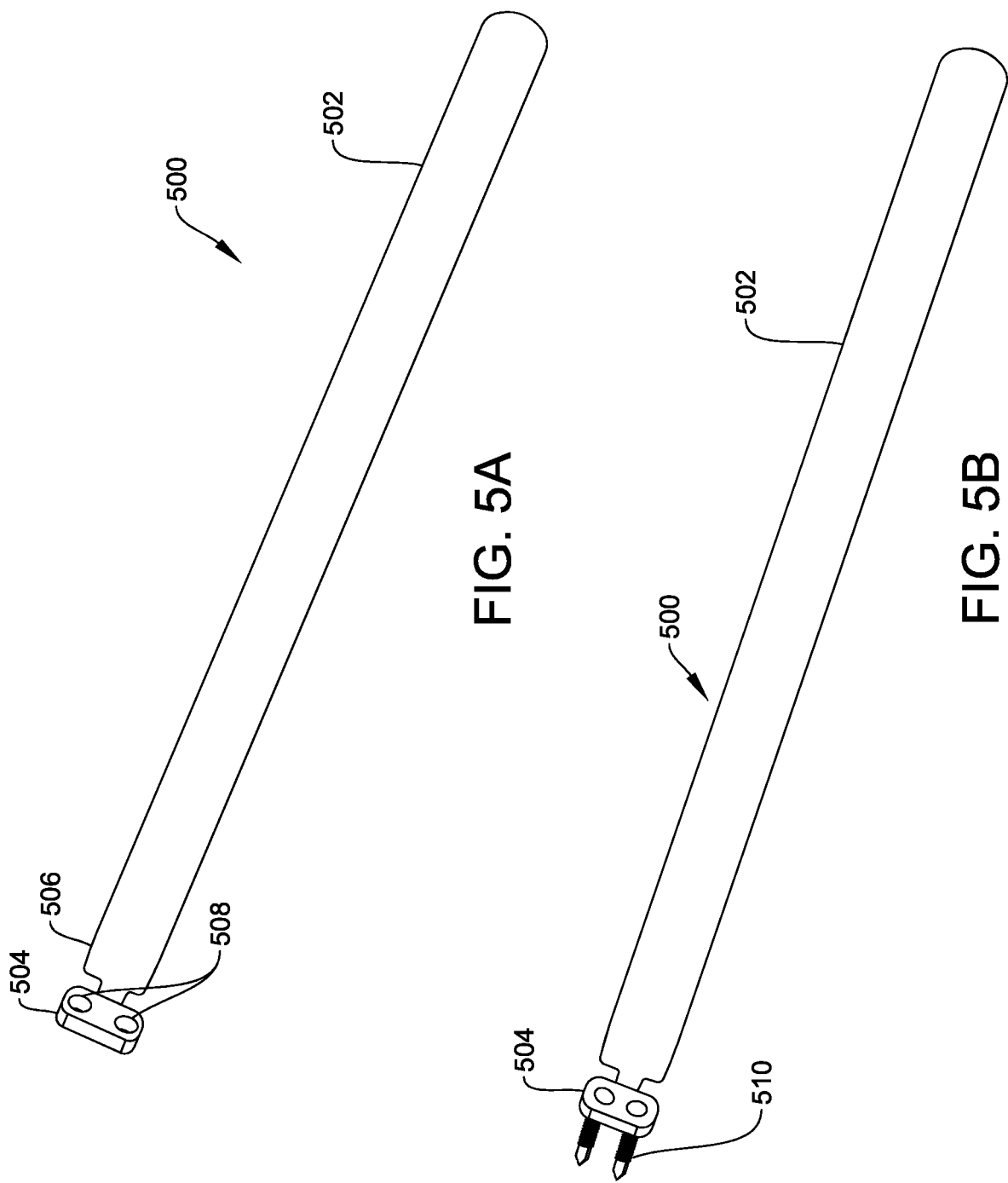

SPINAL SCREW HANDLING

FIELD

Methods and devices are provided for handling and delivering spinal screws.

BACKGROUND

The use of anterior and posterior plates for stabilization and immobilization of the cervical spine is known. A typical posterior plate has a narrow, elongated configuration with a series of spaced holes through which screws are inserted to fix the plate to the vertebrae. A pair of posterior plates is often placed across the lateral posterior surfaces of a set of sequential cervical bones and is secured to the bone using one screw or more per vertebra, thereby preventing the bones from moving relative to one another in either the vertical or horizontal planes.

One concern with screws being implanted in of the cervical spine is that there are sensitive and important structures adjacent to the bony structures, such as nerves and other soft tissue, which, because of their proximity to the implant, may be damaged by insertion or dislocation of screws. In the cervical spine, the vertebral arteries are disposed anterior of lateral masses or lamina and comprise critical structures which cannot be compromised. In addition, the facet joints which provide natural coupling of sequential bones together must also be avoided if possible. Avoidance of these bodies has been a critical and ongoing concern with respect to posterior screw insertion. Moreover, space constraints both within the cervical spine and as a result of the small access port, as well the relatively small size of the screws implanted in the cervical spine, can make it challenging to handle and deliver the screws through the posterior plates.

Accordingly, a need exists for facilitating handling and delivery of screws to spinal plate.

SUMMARY

Various methods and devices are provided for handling and delivering bone screws. In one embodiment, a screw delivery instrument is provided and includes a guide member having a shaft with an inner lumen extending therethrough between a proximal opening and a distal opening. A screw magazine movably coupled to the proximal portion of the guide member and has a plurality of holes extending therethrough. Each hole can be configured to retain a spinal screw, and the screw magazine can be movable relative to the guide member such that each of the plurality of holes in the screw magazine can be aligned with the proximal opening in the shaft to allow a spinal screw retained within a hole to be delivered into the proximal opening and through the inner lumen of the shaft. The instrument can also include a handle coupled to a proximal portion of the guide member.

In one embodiment, the guide member can have a support platform extending radially outward from a proximal end of the shaft. The screw magazine can be movably mounted on the support platform. The handle can also be mated to the support platform.

The screw magazine can have a variety of configurations. In one embodiment, the screw magazine can have an elongate rectangular configuration with the plurality of holes being longitudinally aligned therealong. The screw magazine can be linearly slidable relative to the guide member. In other embodiments, the screw magazine can be cylindrical with the holes being positioned circumferentially therearound. The screw magazine can be rotatable relative to the guide member.

In other aspects, each of the plurality of holes in the screw magazine can have a size that is configured to prevent passage of a screw disposed therein through a proximal opening thereof, and that is configured to allow passage of a screw disposed therein through a distal opening thereof. For example, the distal opening can be larger than the proximal opening.

The instrument can also include any number of screw magazines. For example, the instrument can include at least one additional screw magazine movably coupled to the guide member and having a plurality of holes extending therethrough, with each hole being configured to retain a spinal screw. The at least one additional screw magazine can similarly be movable relative to the guide member such that each of the plurality of holes in the at least one additional screw magazine can be aligned with the proximal opening in the shaft to allow a spinal screw retained within a hole to be delivered into the proximal opening and through the inner lumen of the shaft.

In another embodiment, a spinal implant kit is provided and includes a plate having a plurality of holes spaced longitudinally therealong, a delivery tool, and a driver. The delivery tool can have an elongate shaft with an inner lumen extending therethrough, and a magazine having a plurality of holes formed therein. Each hole can have one of a plurality of screws disposed therein, and the magazine can be movably disposed relative to the elongate shaft such that each of the plurality of holes can be aligned with the inner lumen of the elongate shaft for allowing the screw disposed within the hole that is aligned with the inner lumen to be delivered through the inner lumen to one of the plurality of holes in the plate. The driver can be insertable through the inner lumen of the elongate shaft and can have a drive feature on a distal end thereof for engaging a corresponding drive feature on each of the plurality of screws for driving the screw through one of the plurality of holes of the plate and into bone.

The magazine can have a variety of configurations. In one embodiment, the magazine can be movable along a linear axis, or it can be rotatable relative to the elongate shaft. In other aspects, the magazine can include a plurality of magazines. Each of the plurality of holes in the one or more magazines can have a proximal opening that prevents passage of the screw disposed within the hole, and a distal opening that allows passage of the screw disposed within the hole.

In other aspects, the plurality of screws in the magazine can differ in size relative to one another.

The delivery tool can also have a variety of configurations, and in one embodiment it can include a support platform coupled to a proximal end of the elongate shaft. The magazine can be movably mounted on the support platform. The tool can also include a handle coupled to the support platform.

Methods for delivering a bone screw are also provided, and in one embodiment the method can include positioning a spinal plate having a plurality of holes therein along a spinal column, positioning a shaft of a delivery tool in alignment with one of the plurality of holes in the plate, and moving a magazine on the delivery tool to align one of a plurality of holes in the magazine with a proximal opening of an inner lumen extending through the shaft of the delivery tool. The one of the plurality of holes can have a screw disposed therein. The method can further include advancing a driver through the one of the plurality of holes and through the inner lumen to advance the screw through a distal opening of the inner lumen and through the hole in the plate that is aligned with the shaft, and manipulating the driver to drive the screw into a vertebra of the spinal column, thereby securing the spinal plate to the spinal column.

In certain aspects, moving the magazine can include one of rotating the magazine and linearly sliding the magazine.

In other embodiments, the method can include positioning the shaft in alignment with a second one of the plurality of holes in the plate, and moving the magazine on the delivery tool to align a second one of a plurality of holes in the magazine with the proximal opening of the inner lumen extending through the shaft. The second one of the plurality of holes can have a second screw disposed therein. The method can further include advancing the driver through the second one of the plurality of holes and through the inner lumen to advance the second screw through the distal opening of the inner lumen and through the second hole in the plate that is aligned with the shaft, and manipulating the driver to drive the second screw into the vertebra thereby further securing the spinal plate to the spinal column.

In other embodiments, the method can include detaching the magazine from the delivery tool, and attaching a second magazine to the delivery tool. The second magazine can have a plurality of holes formed therein and each hole having a screw retained therein.

BRIEF DESCRIPTION OF THE DRAWINGS

The invention will be more fully understood from the following detailed description taken in conjunction with the accompanying drawings, in which:

FIG. 1B is another perspective view of the tool of FIG. 1A;

FIG. 1C is another perspective view of the tool of FIG. 1A;

FIG. 1F is another perspective view of the tool of FIG. 1A;

FIG. 4C is a cross-sectional view of the tool of FIG. 4A, including a magazine coupled thereto;

FIG. 4D is an additional cross-sectional view of the tool of FIG. 4A, showing a screw being delivery through the magazine;

FIG. 4E is an additional cross-sectional view of the tool of FIG. 4A, showing the screw ready for delivery into body;

FIG. 4F is an additional cross-sectional view of the tool of FIG. 4A, showing the screw delivering and a second screw passed from the magazine and into the tool for delivery to bone, in use;

FIG. 5A is a side view of another exemplary embodiment of a spinal screw handling and delivery tool; and FIG. 5B is an additional side view of the tool of FIG. 5A, with a plurality of spinal screws installed thereon.

DETAILED DESCRIPTION

Figure 1A:
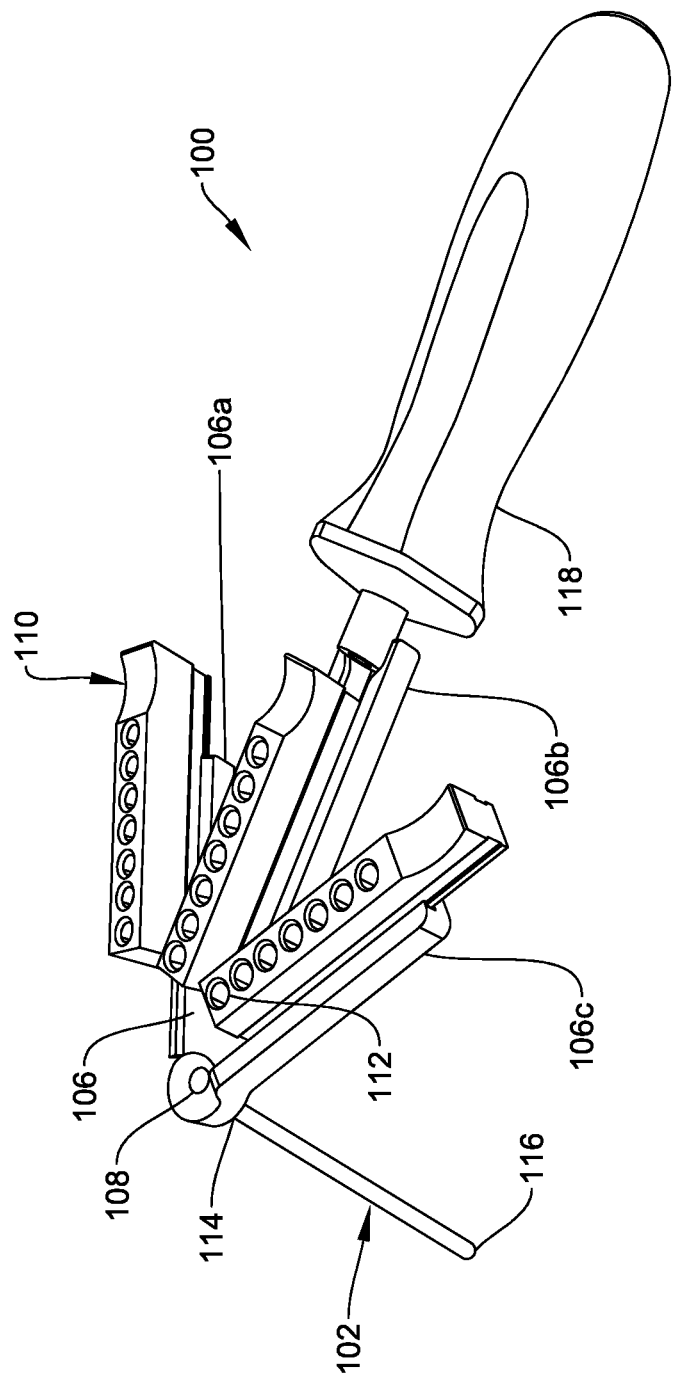
FIG. 1A is a perspective view of a one exemplary embodiment of a spinal screw handling and delivery tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for delivering spinal screws to an implant site. In general, a handheld tool is provided having a guide member with a lumen formed therein that is configured to deliver a spinal screw to an implant, such as a bone plate. The tool can include a storage component, such as a magazine, that is configured to hold multiple spinal screws to allow each screw to be delivered to an implant during a surgical procedure. The tool is also configured to receive a driver for allowing the bone screw to be driven in bone, thereby securing the implant to bone. Such a tool simplifies the screw delivery process, when compared with existing devices and methods, and allows for improved precision in delivering a spinal screw to an implant site. In addition, the tool allows for a reduced number of transfers of the tool between the operating table and the implant site.

FIGS. 1A-1F show one exemplary embodiment of a spinal screw handling and delivery tool 100. As shown, the tool 100 has a guide member that includes an elongate shaft 102 having a lumen extending longitudinally therethrough between a proximal opening 108 and a distal opening (not shown). The guide member can further include a support platform 106 coupled to a proximal end 114 of the elongate shaft 102 and configured to support one or more magazines 110. Each magazine 110 can have a plurality of through-holes 112 configured to retain at least one spinal screw therein, and each magazine 110 can be slidably mounted on the support platform 106 to allow the through-holes 112 to be selectively aligned with the proximal opening 108. A user can thus slide the magazine 110 to align one of the magazine through-holes 112 with the proximal opening 108 of the lumen, at which point a spinal screw disposed within the magazine through-hole 112 can drop from the magazine 110, through the proximal opening 108, and into the elongate shaft 102 for delivery to an implant. The elongate shaft 102 can also be configured to receive a driver therethrough, thus allowing a driver to engage and drive the bone screw into bone for securing an implant to bone.

The elongate shaft 102 can have a variety of shapes and sizes, but in the illustrated embodiment it is in the form of a hollow tube with a substantially circular cross-section. The elongate shaft 102 can be sized to receive a spinal screw through the inner lumen extending therethrough, as well as a spinal screw driver 120, as shown in FIG. 1C. The shaft 102 can have a proximal end 114 that is coupled to the support platform 106 such that the proximal opening 108 is formed in a proximally-facing surface of the support platform 106, as shown in FIG. 1A. The shaft 102 can have a distal end 116 that is configured to be positioned adjacent to an implant, such as a bone plate, for guiding a bone screw into aligned with a thru-hole in the bone plate. The length of the shaft 102 can vary, but preferably it has a length that allows the distal end 116 to be positioned adjacent to a bone plate implanted in bone, e.g., in a cervical vertebra, while the proximal end 114 remains external to the patient for enabling a user to grasp and manipulate the tool 100.

The support platform 106 can also have a variety of configurations, but is preferably configured to support one or more magazines 110 in a manner that allows the magazine(s) 110 to deliver one or more bone screws into the proximal opening 108. While the support platform 106 can have a variety of shapes and sizes, in the illustrated embodiment, as shown in FIG. 1A, the support platform 106 is generally arrow-shaped with three extension arms 106a, 106b, 106c with a magazine 110 coupled to each extension arm of the platform, as will be discussed in more detail below. Such a configuration allows each magazine 110 to have an initial position that is spaced apart and offset from the proximal opening 108, as shown, and to be moved into a delivery configuration in which any one of the through-holes 112 in any one of the magazines 110 is aligned with the proximal opening 108 for delivering a screw therethrough, as will also be discussed in more detail below. While FIGS. 1A-1B illustrate a support platform 106 that allows the magazines 110 to be positioned off to one side of the shaft 102, the support platform 106 can have a variety of other shapes and sizes.

Figure 1D:
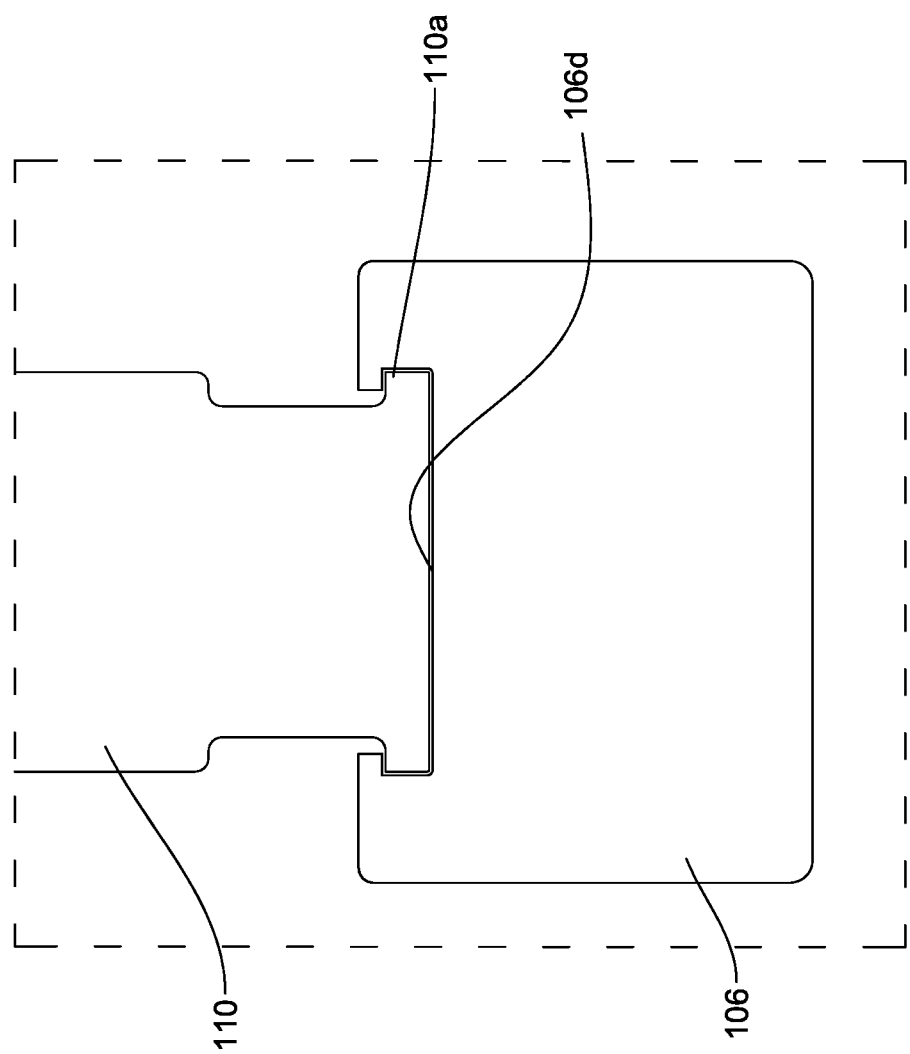
FIG. 1D is an end view of a magazine and a support platform of the tool of FIG. 1A.

Each magazine 110 can also have a variety of configurations, but as indicated above each magazine 110 is configured to retain one or more spinal screws therein prior to delivery to a surgical site. In the illustrated embodiment, shown in FIGS. 1A-1B, three magazines 110 are provided, however the tool can include any number of magazines 110. Each magazine 110 is in the form of an elongate substantially rectangular housing such that it can be mounted on and extend along one of the arms of the support platform 106. However, other magazine housing shapes are possible (e.g., cylindrical, trapezoidal, square, T-shaped, etc.). Each magazine 110 can be oriented along an axis that intersects the proximal opening 108. Such a configuration allows the through-holes 112 to be positioned in alignment with the proximal opening 108. In order to allow Each for alignment of the through-holes 112 with the proximal opening 108, each magazine 110 can be slidably coupled to the support platform 106 such that the magazines 110 slide between the initial configuration, shown in FIG. 1A, and the delivery configuration, as shown for one of the magazines in FIG. 1B. While various techniques can be used to slidably mate the magazines 110 to the support platform 106, in the illustrated embodiment each magazine has a rail, such as 110a formed on a bottom surface thereof that is received within a groove or channel 106d formed in the support platform 106, as shown in FIGS. 1B and 1D. This tongue-and-groove connection allows the magazines to slide along the support platform 106. As shown, the magazines can linearly slide along the support platform. However, in some implementations, the magazines can slide in a non-linear direction along the support platform (e.g., along a curve). Each groove or channel on the support platform 106 can have an open end 106e allowing the magazines 110 to be loaded therein and to be removed as needed.

As previously mentioned, the magazines 110 can each include a plurality of magazine through-holes 112 that are each configured to retain a spinal screw therein. The quantity of through-holes 112 can vary, and the magazine through-holes 112 can be arranged in various configurations. In the illustrated embodiment, each magazine 110 has seven through-holes 12 that are aligned linearly and spaced along the length of the magazines 110 substantially equidistant from one another. Such a configuration allows each through-hole 112 to be sequentially aligned with the proximal opening 108 as the magazine 110 is advanced along the support platform 106 toward the opening 108.

The through-holes 112 can be arranged to retain spinal screws having the same or varying sizes. For example, in one embodiment a first magazine can retain spinal screws all having a first size. A second magazine can retain spinal screws all having a second size that differs from the first size. A third magazine can retain spinal screws all having a third size that differs from both the first and second sizes. Such a configuration will allow a surgeon to select a magazine containing screws of a desired size. In other embodiments, each magazine 110 can retain spinal screws of varying sizes and types (e.g., Torx, slotted). The spinal screws and/or the magazine can be color-coded to provide an indicator of differing dimensions or properties. In some embodiments, each magazine 110 can retain spinal screws of different bone thread configurations (e.g., cortical or spongiosa). In yet other embodiments, each magazine 110 can retain spinal screws of having the same or varying lengths.

Figure 1E:
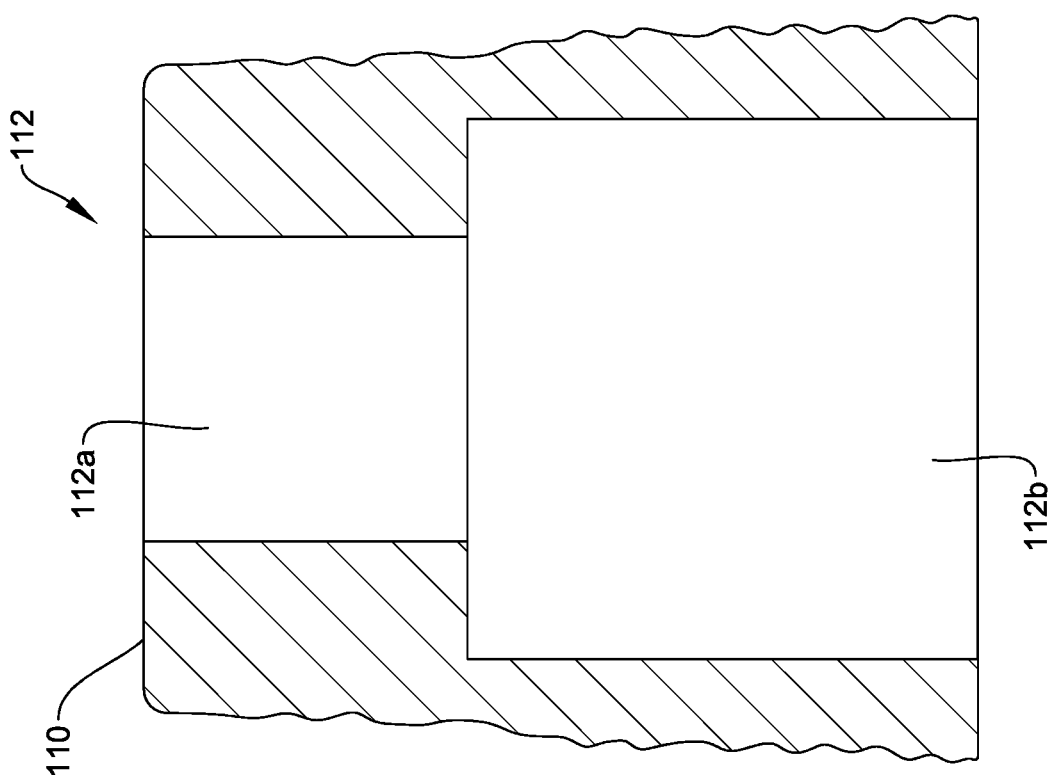
FIG. 1E is a cross-sectional view of the magazine of the tool of FIG. 1A.

Each of the magazine through-holes 112 can include a top portion 112a, open to the top side of the magazine 110, with a first diameter, and a bottom portion 112b, open to the bottom side of the magazine 110, with a second diameter, as shown in FIG. 1E. The second diameter can be larger than the diameter of a spinal screw, such that each of the holes 112 can be loaded with a spinal screw through the bottom side of the magazine 110, and the first diameter can be smaller than the diameter of the loaded spinal screw so as to prevent the loaded spinal screw from passing through the top side of the magazine 110. When the magazine 110 is mounted on the support platform 106, as shown in FIGS. 1A and 1B, the support platform 106 can block the bottom side of the magazine 110, and thereby preventing the screws from following out of the bottom side of the magazine 110.

Referring back to FIG. 1B, in use, a user can deliver a spinal screw 119 retained in the holes 112 of the magazine 110 to an implant site by sliding the magazine 110 from the initial position, shown in FIG. 1A, toward the proximal opening 108. As the magazine 110 is slid across the support platform 106 such that the first through-hole 112 aligns with the proximal opening 108, the spinal screw retained within the through-hole will fall out of the magazine 110 and into the proximal opening 108 in the proximal end 114 of the elongate shaft 102 for delivery to the implant site at the distal end 116 of the elongate shaft 102. In other implementations, the magazine 110 can include a release mechanism (not shown), such as a blocking member that selectively blocks the proximal opening 108, that can be actuated to permit the spinal screw to fall through the proximal opening 108. In yet other implementations, the magazine 110 can include a breakable foil (not shown) applied to the top and/or bottom surfaces of the magazine that can retain the spinal screw within one of the holes 112. In such an embodiment, once a hole 112 is aligned with the proximal opening 108, the user can insert a spinal screw driver 120 into the aligned hole 112 to perforate the foil on the top and/or bottom surface of the magazine 110 and drive the screw through the foil, thereby permitting the spinal screw to fall through the proximal opening 108. In still other implementations, the holes 112 of the magazine can each include a retaining ring (not shown) formed on an interior cylindrical surface of each of the holes 112. The retaining ring can be positioned such that a spinal screw loaded into each hole 112 is prevented from passing through the top side of the magazine 110.

After the spinal screw has been delivered into the lumen in the elongate shaft 102, the magazine 110 can be slid back to its initial position to permit a user to insert the spinal screw driver 120 into the proximal opening 108 and through the elongate shaft 102 to thereby drive the spinal screw into an implant. In other embodiments, the driver can be inserted through the hole 112 in the magazine 110 while it is positioned over through-hole 108, without the need to slide the magazine 110 away from the proximal opening 108, as shown in FIG. 1F. With such a configuration, the driver can have a shaft diameter that is less than the first diameter of the hole 112 at the top side of the magazine 110.

Referring back to FIG. 1A, the tool 100 can also include a handle 118 that facilitates grasping of the tool by a user when the device is in use. The handle 118 can have a variety of configurations. In the illustrated embodiment, the handle 118 has a generally elongate cylindrical configuration and is coupled to one end of one of the extension arms of the support platform 106, as shown in FIG. 1A. However, it can be coupled to the tool 100 at any portion of the tool.

Figure 2B:
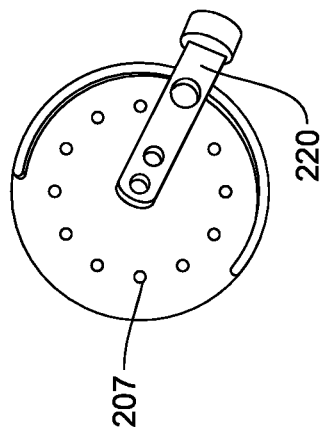
FIG. 2B is another top view of the platform of the tool of FIG. 2A.
Figure 2C:
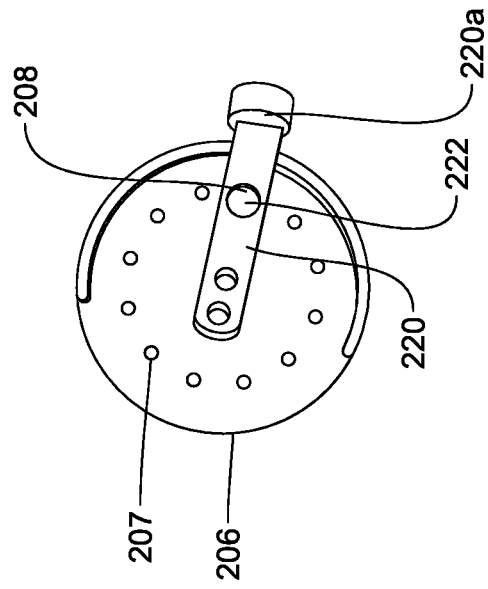
FIG. 2C is an additional perspective view of the platform of the tool of FIG. 2A.
Figure 2A:
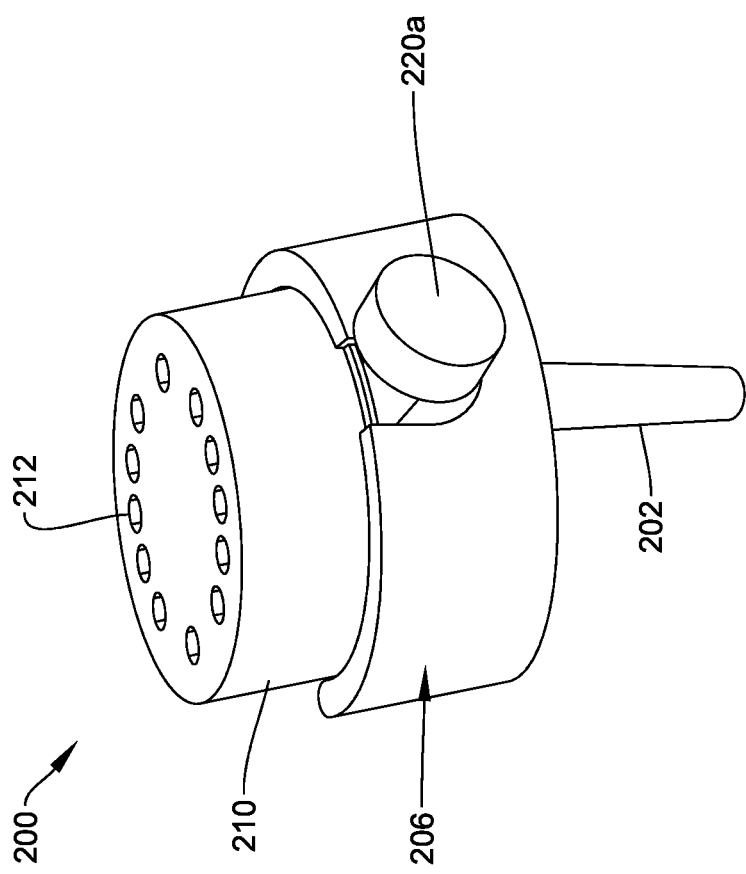
FIG. 2A is a top view of another exemplary embodiment of a spinal screw handling and delivery tool.

FIGS. 2A-2C show another embodiment of a spinal screw handling and delivery tool 200 having an elongate shaft 202 with a platform 206 coupled to a proximal end thereof for supporting a magazine. In this embodiment, the platform 206 is circular or cylindrical for seating a cylindrical magazine 210, thus allowing the magazine 210 to rotate about the platform 206, rather than slide linearly as with tool 100. In particular, the illustrated platform 206 is in the form of a cylindrical housing that is mounted at an offset position to the elongate shaft 202, such that the elongate shaft 202 is positioned adjacent to a perimeter of the platform 206. As shown in FIGS. 2B and 2C, the platform 206 can include a hole extending therethrough and aligned with the lumen in the shaft 202, such that the platform 206 has a proximal opening 208, similar to opening 108 in tool 100. The platform 206 can also include a plurality of indentations 207 spaced around a perimeter of a top surface of the platform 206. The magazine can include a protrusion (not shown) on a lower surface thereof that is sized to be received within each of the plurality of indentations 208. As such, when a user is rotating the magazine 210 relative to the platform 206, the protrusion will extend into one of the plurality of indentations 207 to provide a tactile confirmation to the user that one of the magazine through-holes 212 (explained in further detail below) is concentrically aligned with the proximal opening 208. In some implementations, the spinal screws loaded into the magazine can extend into the plurality of indentations 207 and similarly provide the tactile confirmation of concentric alignment of the one of the magazine through-holes 212 and the proximal opening 208.

As shown, the magazine 210 is mounted on the upper surface of the platform 206 and features a series of through-holes 212 arranged in a circular pattern. Each of the through-holes 212 can be similar to through-holes 112 described above, and is configured to retain a spinal screw and to align with the platform opening 208 when rotated. To deliver a spinal screw, a user can rotate the magazine until a through-hole 212 containing the spinal screw is aligned with the proximal opening 208 in the platform 206, at which point the spinal screw can exit the bottom side of the magazine 210 and drop into the lumen of the elongate shaft 202 for delivery to the implant site. In some implementations, the through-holes 212 can be arranged such that the tips of the spinal screws inserted therein are facing radially outward.

As shown in FIGS. 2B and 2C, in some implementations, the platform can include a release mechanism 220 that is configured to prevent a spinal screw from exiting the bottom side of the magazine 210 through the platform proximal opening 208. FIG. 2B shows the position of the release mechanism 220 when the mechanism is in the closed, blocking position. A user can actuate the release mechanism by pressing inward on the button 220a, as shown in FIG. 2C. In doing so, the user pushes the release mechanism 220 radially inward such that the platform through-hole 208 aligns with a release mechanism through-hole 222, thereby allowing a screw to pass therethrough. While FIGS. 2B and 2C illustrate a release mechanism that moves linearly to slide between blocking and unblocked positions, the release mechanism can have a variety of other configurations and can rotate or move in other directions in order to unblock the opening.

Figure 3B:
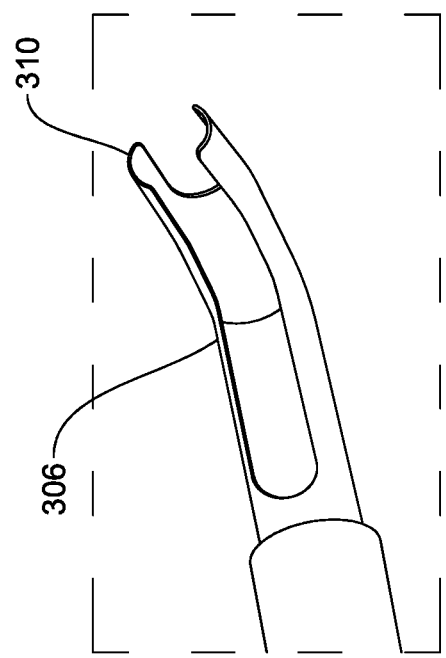
FIG. 3B is a perspective view of a distal end of the tool of FIG. 3A.
Figure 3A:
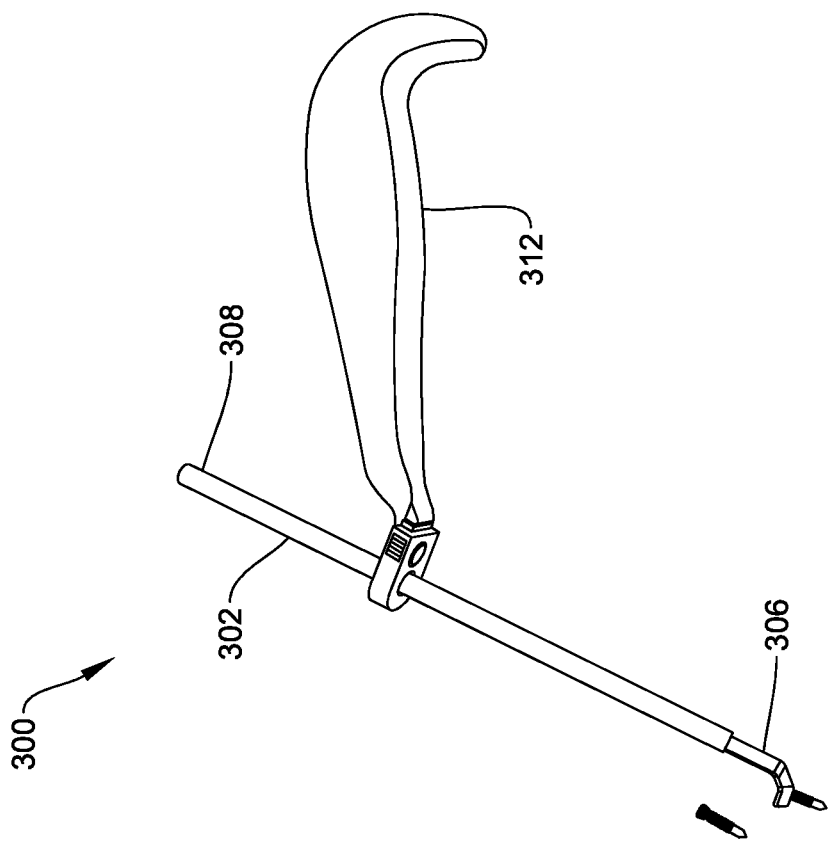
FIG. 3A is a side view of another exemplary embodiment of a spinal screw handling and delivery tool.
Figure 3D:
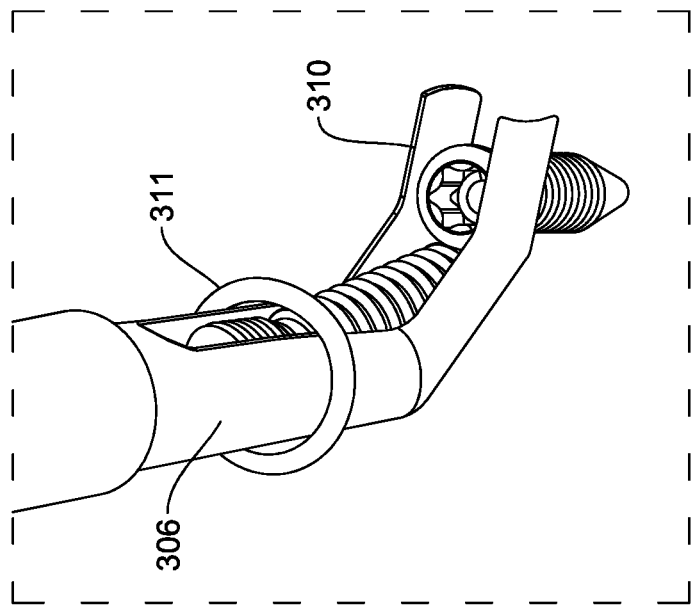
FIG. 3D is an additional perspective view of the distal end of the tool of FIG. 3A, including a retaining ring.
Figure 3C:
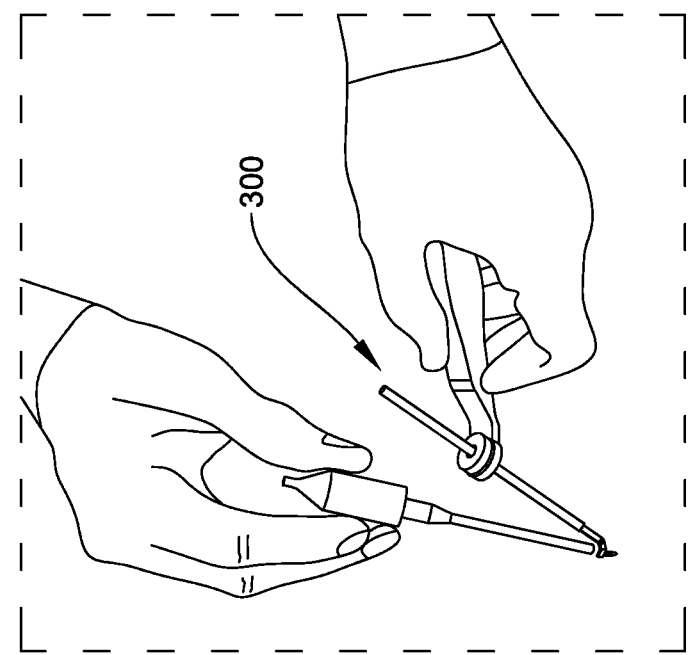
FIG. 3C is a perspective view of the tool of FIG. 3A in use.
Figure 3F:
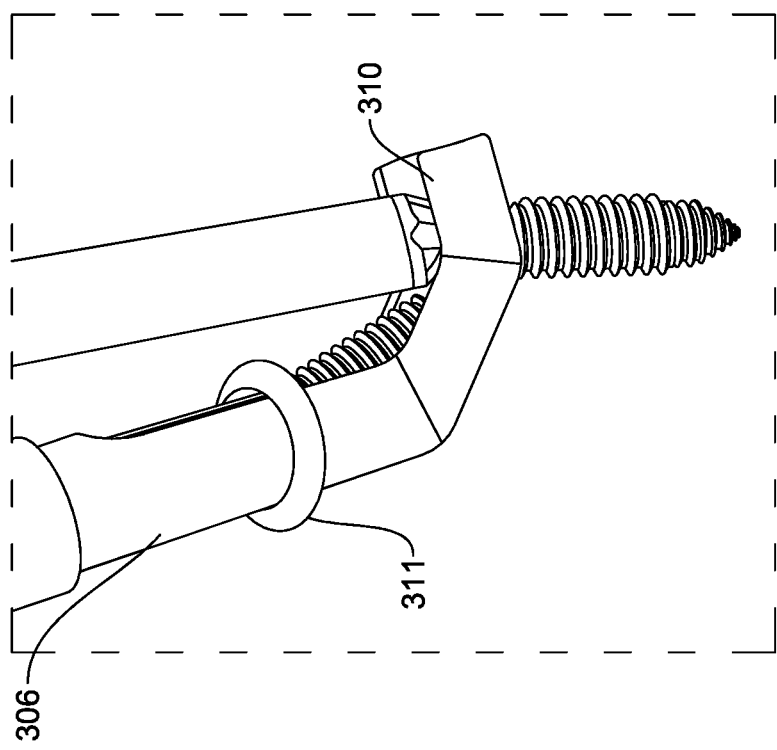
FIG. 3F is an additional perspective view of the distal end of the tool of FIG. 3A, including a retaining ring.
Figure 3E:
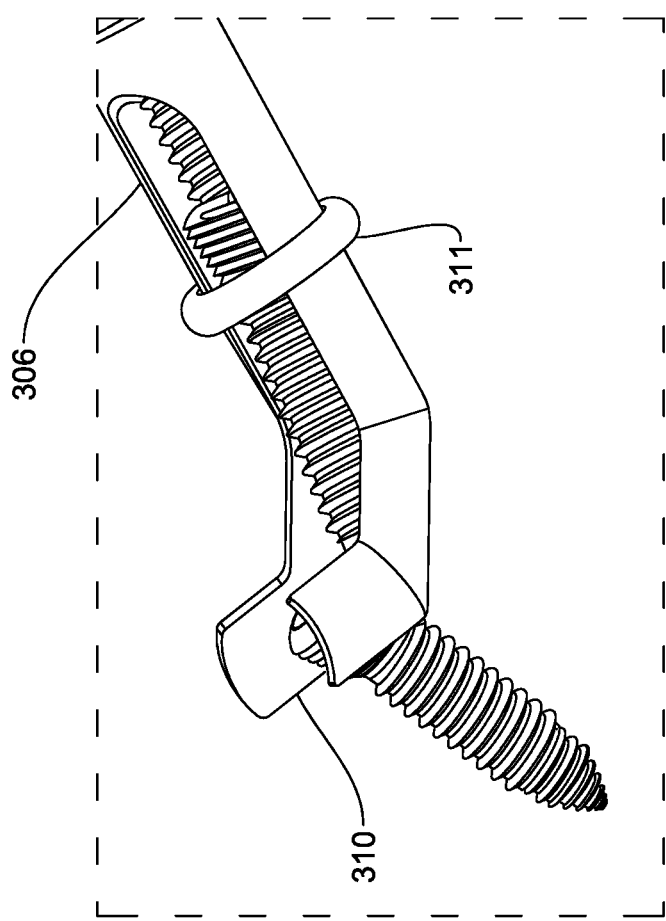
FIG. 3E is an additional perspective view of the distal end of the tool of FIG. 3A, including a retaining ring.

FIGS. 3A-3F show another embodiment of a spinal screw handling and delivery tool 300 having a guide member with an elongate shaft 302 having a lumen extending therethrough from a proximal end 308 to a distal end 306. The tool 300 is similar to tool 100 of FIGS. 1A-1F, however in this embodiment spinal screws can be loaded directly into the lumen at the proximal end 308 of the elongate shaft 302, rather than into a magazine, as with tool 100. The screws can be loaded such that they arrive at the distal end 306. As shown in FIG. 3B, the distal end 306 is bent or curved at two locations and has a two-pronged fork 310 extending at an approximately perpendicular angle to the longitudinal axis of the elongate shaft. The fork 310 can be configured to seat and engage a head of a spinal screw. When the loaded spinal screws are inserted into the lumen and arrive at the distal end 306, the leading screw will slide into the space between the two prongs of the fork 310, thereby allowing a user to supply a screw driver alongside the elongate shaft 302 to drive the screw at the implant site, as shown in FIGS. 3C and 3F. Any screws seated behind the leading screw will be retained within the shaft just proximal of the bend and are prevented from moving distally into the fork 310 by the leading screw. Thus, once the leading screw is delivered, a subsequent screw can fall down into the fork 310 for delivering into bone. As further shown in FIGS. 3D-3F, the tool 300 can include a retaining ring 311 that is configured to facilitate retention of the screws seated behind the leading screw. The retaining ring 311 can be sized to fit around the distal end 306 of the elongate shaft 302.

As further shown in FIG. 3A, the tool 300 can include a handle 312 coupled to the elongate shaft 302 to facilitate grasping and manipulation of the device. The handle 312 can extend at an angle relative to the elongate shaft 302 so that it does not interfere with use of a driver. As shown, in the illustrated embodiment the handle 312 is coupled to the elongate shaft at a distance from the proximal end, however the handle can be positioned at any location. Moreover, the handle can have various configurations.

FIGS. 4A-4F show another embodiment of a spinal screw handling and delivery tool 400 having a guide member with an elongate shaft 402 having a lumen extending therethrough. In this embodiment, the shaft 402 has a proximal portion 408 with a diameter that is larger than a diameter of a distal portion 406. The proximal portion 408 can include an opening or window 410 formed in a sidewall thereof adjacent to the distal end thereof for allowing a spinal screw to be loaded directly into the lumen. The window is in the form of an elongate cut-out in the sidewall of the elongate shaft having a size that allows a screw to pass therethrough. As will be described in further detail, in some implementations, a magazine 414 could be coupled to the window 410 such that spinal screws can be automatically loaded into the elongate shaft 402 without the need for the user to manually load the spinal screws into the elongate shaft 402.

Figure 4A:
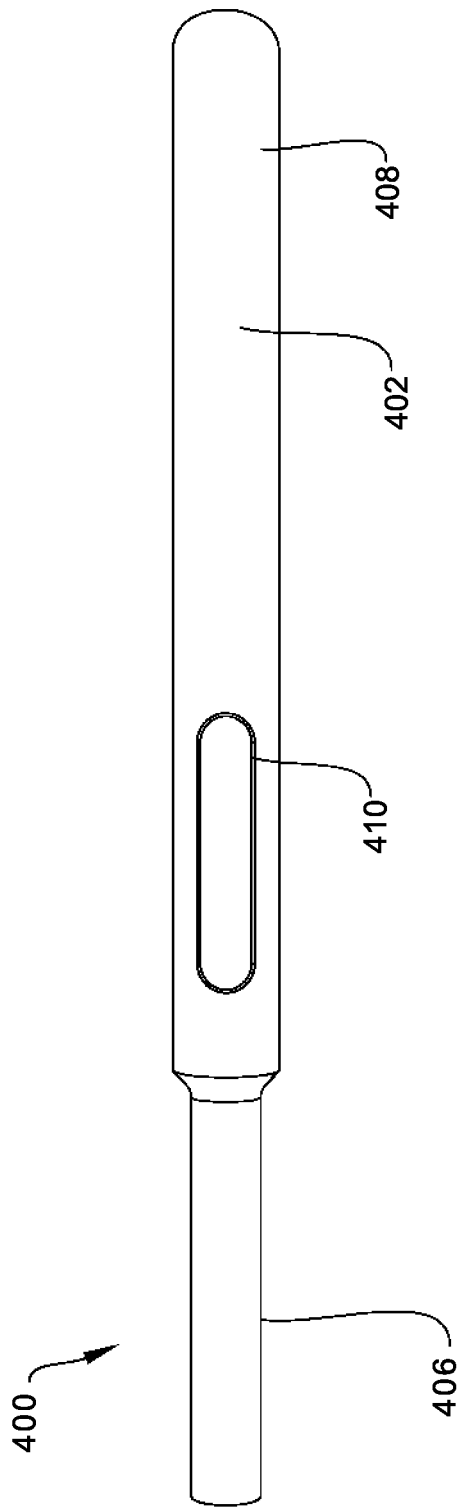
FIG. 4A is a side view of a spinal screw handling and delivery tool according to another embodiment.
Figure 4B:
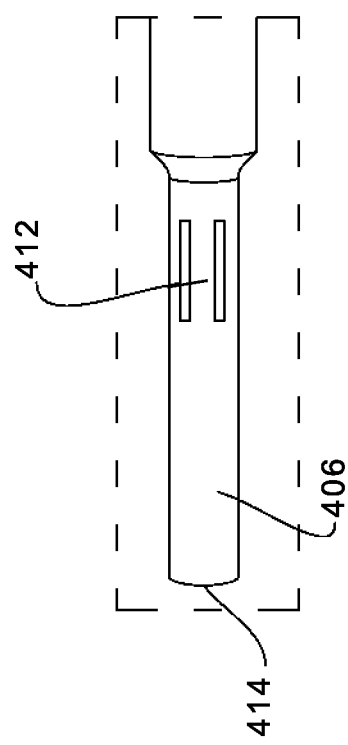
FIG. 4B is a side view of a distal end of the tool of FIG. 4A.

Once a screw is passed through the window 410 and into the inner lumen, the screw will drop down the shaft toward the distal end of the device. To prevent the screw from falling out of the distal end, the distal portion 406 can include an engagement feature, such as a deflectable retention tang 412, that extends into the lumen, as shown in FIG. 4B. The deflectable retention tang 412 can be configured to block distal movement of the spinal screw to retain the screw within the elongate shaft 404. In the illustrated embodiment, the tang 412 is formed from two linear cut-outs in the sidewall, with the tang 412 being deformed into the lumen. In other embodiments, the tang can be formed separate from and mated to the elongate shaft. Other techniques can also be used to selectively block distal movement of a screw through the lumen of the elongate shaft.

In use, when a loaded spinal screw is inserted through the window 410, the loaded spinal screw is located proximal of the deflectable retention member 412. The screw will move distally until it encounters the deflectable tang 412. In order to move the screw past the tang 412, a spinal screw driver can be inserted into the proximal end 416 of the elongate shaft 402 and advanced into engagement with the screw. A distal force applied by the screw driver will cause the deflectable tang 412 to deflect radially outward, thus allow the screw and the screw driver to move distally past the tang. The user can thereby deliver the spinal screw to the implant site and drive the spinal screw into bone.

Referring to FIGS. 4C-4F, as previously mentioned, in some implementations, a magazine 414 configured to retain a plurality of spinal screws 418 can be coupled to the window 410 such that the plurality of spinal screws 416 can be easily loaded into the elongate shaft 402 without the need for the user to manually load each spinal screw into the elongate shaft 402. As shown in FIG. 4C, the magazine 414 can include a lumen extending therethrough and a distal magazine window 414a that is configured to permit a spinal screw 416 to be transferred from the magazine 414 to the elongate shaft 402, through the window 410. As shown in FIGS. 4C-4D, entry of one of the plurality of spinal screws 416 can be regulated by the position of a spinal screw driver 420. For example, as shown in FIG. 4C, when the spinal screw driver 420 is advanced into the distal portion 406 of the elongate shaft 402, the spinal screws 418 are prevented from passing through the magazine window 414a and the window 410 in the elongate shaft 402. However, once the spinal screw driver 420 is removed from the distal portion 406 of the elongate shaft, as shown in FIG. 4D, the spinal screw driver 420 can be slid proximally to permit one of the plurality of spinal screws 418 to pass through the magazine window 414a and the window 410 in the elongate shaft 402. Once the spinal screw 418 enters the elongate shaft, the screw 418 will move distally until it encounters the deflectable tang 412, as shown in FIG. 4E. In order to move the screw past the tang 412, the spinal screw driver 420 can be re-inserted into the distal portion 406 of the elongate shaft 402 and advanced into engagement with the screw. A distal force applied by the spinal screw driver 420 will cause the deflectable tang 412 to deflect radially outward, thus allow the screw and the screw driver to move distally past the tang, as shown in FIG. 4F. The user can thereby deliver the spinal screw to the implant site and drive the spinal screw into bone.

FIGS. 5A-5B show yet another embodiment of a spinal screw handling and delivery tool 500 having a guide member with an elongate shaft 502 that is configured to deliver a plurality of spinal screws to a spinal implant. In this embodiment, the distal end of the tool 500 is configured to deliver screws in a preconfigured arrangement that corresponds to the arrangement of the screw holes in a spinal implant. In particular, the illustrated elongate shaft 502 has a template 504 coupled to a distal end 506 of the elongate shaft 502. The template 504 includes a plurality of holes 508 for receiving spinal screws 510 (see FIG. 5B). In some implementations, the holes 508 can be oriented and/or spaced such that the hole 508 placement matches the location of screw holes on a spinal implant. In some implementations, the holes 508 may be threaded to match the corresponding threads of a spinal screw, thereby preventing any spinal screws inserted into the template 504 from prematurely separating from the template 504 prior to delivery to an implant site. In other implementations, the template 504 can be made from a deformable material that retains the screws therein, and that allows the screws to pass therethrough when a force is applied to the screws. In yet other implementations, the template 504 can be detachable from the tool 500. While FIGS. 5A-5B illustrate a template configured to seat two screws, the template can have any configuration and can retain any numbers of screws in any arrangement.

In use, a plurality of spinal screws can be retained in the holes 508 of the template for delivery to an implant site. The elongate shaft 502 can be delivered to the implant site and the template can be aligned with a spinal plate. A user can drive the spinal screws through the template 504 and through a bone plate with the use of a spinal screw driver. Once the spinal screws are driven such that they are no longer threaded into the template 504, the tool 500 is removed from the implant site. In implementations where a flexible template is employed, a user can push the loaded spinal screws through the template.

The devices and methods disclosed herein can be used in minimally-invasive surgery and/or open surgery. While the devices and methods disclosed herein are generally described in the context of advancing a bone anchor into a pedicle, it will be appreciated that the methods and devices disclosed herein can be used with any human or animal bone, implant, non-living object, and so forth.

The tools disclosed herein can be designed to be disposed of after a single use, or they can be designed to be used multiple times. In either case, however, the tool can be reconditioned for reuse after at least one use. Reconditioning can include any combination of the steps of disassembly of the tool, followed by cleaning or replacement of particular pieces, and subsequent reassembly. In particular, the tool can be disassembled, and any number of the particular pieces or parts of the tool can be selectively replaced or removed in any combination. Upon cleaning and/or replacement of particular parts, the tool can be reassembled for subsequent use either at a reconditioning facility, or by a surgical team immediately prior to a surgical procedure. Those skilled in the art will appreciate that reconditioning of a tool can utilize a variety of techniques for disassembly, cleaning/replacement, and reassembly. Use of such techniques, and the resulting reconditioned tool, are all within the scope of the present application.

Preferably, the tools and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A screw delivery instrument, comprising:
   a guide member having a shaft with an inner lumen extending therethrough between a proximal opening and a distal opening; and
   a screw magazine movably coupled to the proximal portion of the guide member and having a plurality of holes extending therethrough, each hole having a distal hole opening and an opposite proximal hole opening and being configured to retain a spinal screw such that the spinal screw can only be loaded through the distal hole opening, and the screw magazine being movable relative to the guide member such that each of the plurality of holes in the screw magazine can be aligned with the proximal opening in the shaft to allow a spinal screw retained within the hole to be delivered through the distal hole opening into the proximal opening and through the inner lumen of the shaft.

2. The instrument of claim 1, further comprising a handle coupled to a proximal portion of the guide member.

3. The instrument of claim 1, wherein the guide member has a support platform extending radially outward from a proximal end of the shaft, and wherein the screw magazine is movably mounted on the support platform.

4. The instrument of claim 3, wherein the support platform includes a plurality of indentations spaced around a perimeter of a top surface of the support platform, and wherein the top surface faces a distal surface of the screw magazine.

5. The instrument of claim 4, wherein the screw magazine includes a protrusion that is sized to be received within each of the plurality of indentations and configured to provide a tactile confirmation that one of the plurality of holes is aligned with the proximal opening.

6. The instrument of claim 1, wherein the guide member has a support platform extending radially outward from a proximal end of the shaft, and wherein the screw magazine is movably mounted on the support platform, and a handle is mated to the support platform.

7. The instrument of claim 1, wherein each of the plurality of holes in the screw magazine has a size that is configured to prevent passage of a spinal screw disposed therein through the proximal hole opening, and that is configured to allow passage of a spinal screw disposed therein through the distal hole opening.

8. The instrument of claim 7, wherein the size of each of the plurality of holes in the screw magazine is the same.

9. The instrument of claim 7, wherein the size of each of the plurality of holes in the screw magazine is different from one another.

10. The instrument of claim 7, wherein each of the plurality of holes has a top portion having a first diameter and abutting the proximal hole opening, and a bottom portion having a second diameter and abutting the distal hole opening, and wherein the second diameter is larger than the first diameter.

11. The instrument of claim 1, wherein the screw magazine has an elongate rectangular configuration with the plurality of holes being longitudinally aligned therealong.

12. The instrument of claim 1, wherein the screw magazine is rotatable relative to the guide member.

13. The instrument of claim 1, further comprising a release mechanism that is configured to be actuated to thereby permit a spinal screw to be delivered into the proximal opening.

14. The instrument of claim 13, wherein the release mechanism includes a through-hole, and wherein, when actuated, the release mechanism is displaced such that the through-hole aligns with the proximal opening to allow a spinal screw to be delivered into the proximal opening.

15. The instrument of claim 13, wherein, when actuated, the release mechanism moves linearly from a blocking position, in which the spinal screw is prevented from delivery into the proximal opening, to an unblocked position, in which a spinal screw is permitted to be delivered into the proximal opening.

16. The instrument of claim 13, wherein, when actuated, the release mechanism rotates to permit delivery of a spinal screw into the proximal opening.

17. The instrument of claim 1, wherein each of the plurality of holes includes a retaining ring disposed on an interior cylindrical surface thereof and positioned such that a spinal screw disposed in the hole is prevented from passing through the distal hole opening.

18. A screw delivery instrument, comprising:
   a support platform having a proximally-facing surface that includes at least one channel formed therein, a distally-facing surface positioned distal to and opposite the proximally-facing surface, and an opening extending through the support platform between the distally-facing surface and the proximally-facing surface;
   a guide member having a shaft with an inner lumen extending therethrough between a proximal end and an opposite, distal end, the proximal end positioned on the distally-facing surface of the support platform such that the inner lumen is in fluid communication with the opening of the support platform; and
   a screw magazine disposed on the proximally-facing surface of the support platform and having a plurality of holes extending therethrough, each hole being configured to retain a spinal screw, and the screw magazine having a protrusion configured to couple to the at least one channel of the support platform, the screw magazine being movable relative to the support platform such that each of the plurality of holes in the screw magazine can be aligned with the proximal opening in the shaft to allow a spinal screw retained within the hole to be delivered into the proximal opening and through the inner lumen of the shaft.

19. The instrument of claim 18, wherein the screw magazine has an elongate rectangular configuration with the plurality of holes being longitudinally aligned therealong.

20. A screw delivery instrument, comprising:
- a guide member having a shaft with an inner lumen extending therethrough between a proximal opening and a distal opening;
- a screw magazine movably coupled to the proximal portion of the guide member and having a plurality of holes extending therethrough, each hole being configured to retain a spinal screw, and the screw magazine being movable relative to the guide member such that each of the plurality of holes in the screw magazine can be aligned with the proximal opening in the shaft to allow a spinal screw retained within the hole to be delivered into the proximal opening and through the inner lumen of the shaft; and
- a release mechanism coupled to the screw magazine and configured to slide between a first position in which the proximal opening is blocked by the release mechanism and a second position in which the spinal screw is permitted to be delivered into the proximal opening.

\* \* \* \* \*